US00PP12546P2

(12) United States Plant Patent
Fruehwirth

(10) Patent No.: US PP12,546 P2
(45) Date of Patent: Apr. 16, 2002

(54) POINSETTIA PLANT NAMED 'WINDARK'

(75) Inventor: Franz Fruehwirth, Encinitas, CA (US)

(73) Assignee: Paul Ecke Ranch, Inc., Encinitas, CA (US)

( * ) Notice: Subject to any disclaimer, the term of this patent is extended or adjusted under 35 U.S.C. 154(b) by 0 days.

(21) Appl. No.: 09/087,917

(22) Filed: Jun. 1, 1998

(51) Int. Cl.[7] ..... A01H 5/00
(52) U.S. Cl. ..... Plt./307

(58) Field of Search ..... Plt./307

*Primary Examiner*—Howard J. Locker
*Assistant Examiner*—Kent L. Bell
(74) *Attorney, Agent, or Firm*—C. A. Whealy

(57) ABSTRACT

A new and distinct variety of Poinsettia plant named 'Windark', characterized by its dark red, reflexed flower bracts; dark green, reflexed leaves; freely branching plant habit; relatively strong stems in comparison to other selections with reflexed bracts and leaves; and excellent postproduction longevity.

1 Drawing Sheet

BACKGROUND OF THE INVENTION

The present invention relates to a new and distinct variety of Poinsettia plant, botanically known as *Euphorbia pulcherrima* Willd., and hereinafter referred to by the name 'Windark'.

The new variety is a naturally-occurring branch mutation of the Inventor's proprietary *Euphorbia pulcherrima* Willd. seedling selection code number P-60. The new Poinsettia was selected by the Inventor in a greenhouse in Encinitas, Calif., in the winter of 1995. The objective of the Inventor's Poinsettia development program is to create new Poinsettia cultivars having interesting bract and leaf display, desirable bract and foliage color and form, strong and freely branching stems and good post-production longevity.

Asexual reproduction of the new variety by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Windark'. These characteristics in combination distinguish 'Windark' as a new and distinct variety:

1. Dark red, reflexed flower bracts.
2. Dark green, reflexed leaves.
3. Freely branching plant habit.
4. Relatively strong stems compared to other sections with reflexed bracts and leaves.
5. Excellent postproduction longevity.

In side-by-side comparisons conducted by the Inventor in Encinitas, Calif., plants of the new Poinsettia differed from plants of the seedling selection P-60 in the following characteristics:

1. Plants of the new Poinsettia are more compact than plants of P-60.
2. Primary flower bracts of plants of the new Poinsettia are smaller than primary flower bracts of plants of P-60.
3. Plants of the new Poinsettia are more freely branching than plants of P-60.

BRIEF DESCRIPTION OF THE PHOTOGRAPH

The accompanying colored photograph illustrates the overall appearance of the new variety, showing the colors as true as it is reasonably possible to obtain in colored reproductions of this type. The photograph comprises a side perspective view of a typical plant of 'Windark'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a polyethylene-covered greenhouse with day temperatures about 23° C., night temperatures about 17° C., and light levels about 40,000 lux. Plants were grown in 16.5-cm pots, pinched one time, and flowered under long nyctoperiods.

In the following description, color references are made to The Royal Horticultural Society Colour Chart except where general terms of ordinary dictionary significance are used.

Botanical classification: *Euphorbia pulcherrima* Willd. 'Windark'.

Parentage: Naturally-occurring branch mutation of Inventor's proprietary *Euphorbia pulcherrima* Willd. seedling selection code number P-60.

Propagation:

*Type cutting*.—Terminal cuttings.

*Time to initiate roots*.—Summer: About 12 to 18 days at 27° C. Winter: About 15 to 18 days at 24° C.

*Time to develop roots*.—Summer: About 26 days at 27° C. Winter: About 26 days at 24° C.

*Rooting habit*.—Thick, freely branching, becoming fibrous with development.

Plant description:

*Plant form*.—Inverted triangle, top of plant rounded.

*Growth habit*.—Mostly upright. Freely branching. Branching is enhanced by removing the shoot apex. Moderate vigor and moderate growth rate.

*Plant height*.—About 32 cm.

*Crop time*.—From unrooted cuttings to a flowering plant in a 16.5-cm container, about 18 weeks are required.

*Stem description*.—Thick, strong. Number of lateral branches: About five or six lateral branches are formed after removal of the terminal apex. Lateral branch length: About 24 cm. Stem diameter: About 1.2 cm. Internode length: About 1 cm. Stem color: 146A.

*Foliage description*.—Quantity of leaves per lateral branch: About 14. Length: About 7.5 cm. Width: About 6.75 cm. Shape: Ovate. Apex: Acuminate. Base: Rounded to acute. Margin: Entire and ruffled, ruffling of leaf gives the appearance that leaves are slightly sinuate. Texture: Ruffled, rugose, dull, mostly glabrous with very slight pubescence on lower surface. Aspect: Reflexed, leaves curled backward, leaf apices nearly contact lateral stems. Color: Young foliage, upper surface: Darker than 147A. Young foliage, lower surface: 147B. Mature foliage, upper surface: Darker than 147A. Mature foliage, lower surface: 137B. Venation, upper surface: 147B. Venation, lower surface: 147C. Petiole: Length: About 2 cm. Diameter: About 4 mm, thick. Color: 53A.

Inflorescence description:

*Inflorescence type and habit*.—Inflorescences are compound corymbs of cyathia with colored flower bracts subtending the cyathia. Reflexed bracts give a spherical appearance to the inflorescence.

*Natural flowering season*.—Autumm/winter in Northern Hemisphere. Flower initiation and development can be induced under long nyctoperiod conditions.

*Quantity of inflorescences*.—One per lateral branch, usually about 5 or 6 per plant.

*Inflorescence size*.—Diameter: About 13 cm. Height (depth): About 6 cm.

*Flower bracts*.—Quantity of flower bracts per inflorescence: Usually about 24 primary bracts and about 10 secondary bracts per inflorescence. Length: About 6 cm. Width: About 6 cm. Shape: Ovate. Apex: Abruptly acuminate. Base: Acute. Margin: Entire and ruffled, ruffling of bract gives the appearance that bracts are sinuate. Texture: Ruffled, rugose, smooth, slightly glabrous. Aspect: Reflexed, bracts curled backward similar to leaves. Color: Developing, upper surface: Rosier than 45A. Developing, lower surface: 53C. Mature, upper surface: 45A. Mature, lower surface: 46B.

*Cyathia*.—Quantity: Usually about 18 per corymb. Diameter of cyathia cluster: About 3 cm. Length: About 1.3 cm. Width: About 5 mm. Color: Immature: 144A. Mature: 144B. Peduncle: Length: About 2 mm. Aspect: Strong, erect. Color: 144B. Stamens: Stamen number: Numerous, typically more than 10 per cyathium. Amount of pollen: Moderate. Pollen color: 9A. Pistils: Pistil number: 1 per cyathium. Stigma shape: Rounded, not parted. Stigma color: 45B. Style length: About 1 mm. Style color: 144D. Nectary color: 14A.

Disease resistance: No fungal, bacterial nor viral problems observed on plants grown under commercial conditions.

Postproduction longevity: Generally plants maintain good substance and bract color for about four weeks under interior conditions.

It is claimed:

1. A new and distinct variety of Poinsettia plant named 'Windark', as illustrated and described.

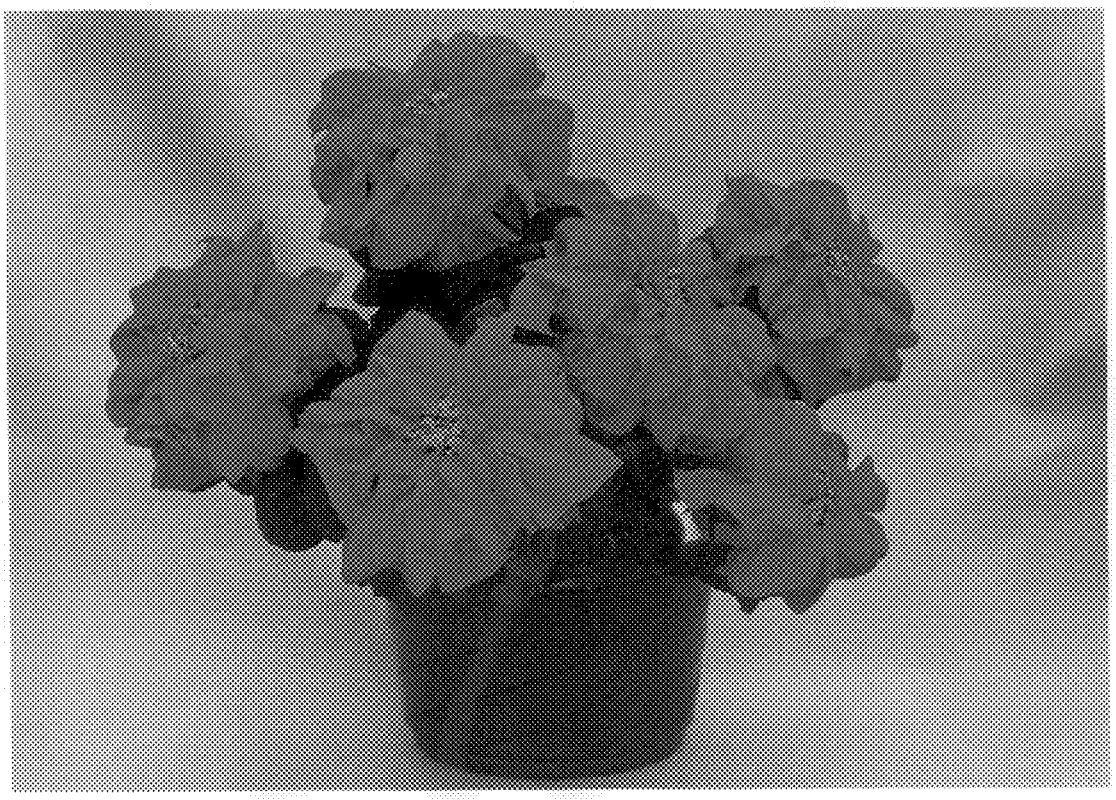

* * * * *